United States Patent [19]

Jackson

[11] Patent Number: 4,890,628

[45] Date of Patent: Jan. 2, 1990

[54] SURGICAL DRAPE WITH MEANS FOR CHANNELING AND COLLECTING FLUIDS

[75] Inventor: Elizabeth M. Jackson, Roswell, Ga.

[73] Assignee: Kimberly-Clark Corporation, Neenah, Wis.

[21] Appl. No.: 128,554

[22] Filed: Dec. 3, 1987

[51] Int. Cl.⁴ .............................................. A61F 13/00
[52] U.S. Cl. ..................................... 128/849; 128/853
[58] Field of Search ................... 128/132 D, 849, 853, 128/854; 604/332, 337, 338, 341, 355, 356, 357, 317, 327

[56] References Cited

U.S. PATENT DOCUMENTS

| | | | |
|---|---|---|---|
| Re. 31,886 | 5/1985 | Hodgson | 428/40 |
| Re. 31,887 | 5/1985 | Hodgson | 428/355 |
| 3,410,266 | 11/1968 | Krzewinski | 128/132 |
| 3,452,750 | 7/1969 | Blanford | 128/132 |
| 3,494,356 | 2/1970 | Melges | 128/132 |
| 3,503,391 | 1/1970 | Melges | 128/132 |
| 3,650,267 | 3/1972 | Anderson | 128/132 |
| 3,677,266 | 7/1972 | Green | 128/132 |
| 3,695,260 | 10/1972 | Endres | 128/132 |
| 3,763,857 | 10/1973 | Scherading | 128/132 |
| 3,791,382 | 2/1974 | Collins | 128/132 |
| 3,797,484 | 3/1974 | Ericson | 128/132 |
| 3,826,253 | 7/1974 | Larsh | 128/132 |
| 3,911,912 | 10/1975 | Kreb | 128/132 |
| 4,051,845 | 10/1977 | Collins | 128/132 |
| 4,169,472 | 10/1979 | Morris | 128/132 D |
| 4,275,720 | 6/1981 | Wichman | 128/132 D |
| 4,378,794 | 4/1983 | Collins | 128/132 |
| 4,414,968 | 11/1983 | Amin | 128/132 D |
| 4,452,845 | 6/1984 | Lloyd | 428/220 |
| 4,462,396 | 7/1984 | Wichman | 128/132 |
| 4,471,769 | 9/1984 | Lockhart | 128/132 |
| 4,489,720 | 12/1984 | Morris et al. | 128/132 D |
| 4,559,937 | 12/1985 | Vinson | 128/132 |
| 4,570,628 | 2/1986 | Neal | 128/132 |
| 4,596,245 | 6/1986 | Morris | 128/132 |
| 4,598,458 | 7/1986 | McAllester | 128/132 D |

FOREIGN PATENT DOCUMENTS 0169316 1/1986 European Pat. Off. .

Primary Examiner—Robert A. Hafer
Assistant Examiner—Charles H. Sam
Attorney, Agent, or Firm—Patrick C. Wilson

[57] ABSTRACT

Disclosed herein is a surgical drape with a fluid collection system for channeling and collecting fluids emanating from the surgical site during an operation. The surgical drape includes a main sheet with a fenestration located therein. A fluid collection bag is attached to the main sheet with its open end positioned adjacent the fenestration. The fluid collection bag has a front panel and a rear panel joined along common side edges to define a fluid receiving chamber. The front and rear panels further form a trough on either side of the bag extending upwardly from the open end along the common side edges. The fluid collection bag, with its integrally formed troughs, is attached to the main sheet such that the troughs and the open end of the fluid collection bag surround at least a portion of the fenestration with the troughs opening inwardly toward the fenestration so as to contain and channel fluids into the open end of the fluid collection bag.

6 Claims, 5 Drawing Sheets

SURGICAL DRAPE WITH MEANS FOR CHANNELING AND COLLECTING FLUIDS

BACKGROUND OF THE INVENTION

The present invention relates to a surgical drape with a fluid collection system for channeling and collecting fluids emanating from the surgical site during an operation.

Numerous operating procedures result in the production of rather large quantities of fluids which are removed from the operating site to facilitate the procedure. The two primary sources of such fluids are the body itself, including blood and other body fluids, and irrigation liquids used to flush the operating site.

Removal of the fluids can be accomplished in a number of ways. One of the oldest methods of controlling fluids is to use absorptive devices such as towels, sponges and pads which have been sterilized to lessen the risk of infection. These absorptive devices are commonly placed around the site of the incision, a technique called "squaring off". Inside the body cavity, additional sponges, etc., may be actually packed within the cavity to absorb liquids and protect organs. Whereas in the past such absorptive devices were reusable items, today they are almost all single use disposable items in an attempt to reduce handling and the risk of infection.

As part of good sterile technique, it is common practice to keep the patient, the operating personnel and the room as clean, dry and bacteria free as possible. This is especially crucial in the control of infectious disease containing fluids such as blood. Should fluids from the operation collect on the floor there is also an increased risk of personnel slipping and falling or suffering from electrical shock. Furthermore, overflows and spills of body fluids result in more time needed for clean-up which decreases the effective utilization of the operating room. As a result, there is a recognized need for a surgical drape which permits the effective channeling and collection of fluids created and/or released during a surgical procedure.

One solution to this problem has been to use suction devices to remove excess fluids from the operating site. Suction may be used alone or in combination with absorptive devices. However, suction is typically used to remove fluids within the body cavity and thus will do little to aid fluid control outside the body cavity.

In certain surgical techniques, particularly those involving the perineal area or the cranium, large amounts of fluid are either released or used due to irrigation. In such cases, absorptive devices and/or suction devices are oftentimes insufficient or impractical for removal of fluids from the operation site. As a result, modifications have been made to the surgical drape itself to help direct and/or collect the fluids. Such modifications have been accomplished by creating folds and tucks in the drapes to form pockets for collecting fluids or by attaching separate pieces of material to the exterior surface of the drape to form pockets for trapping or collecting fluids. Examples of such techniques can be found in Collins U.S. Pat. No. 3,791,382. Unfortunately, such techniques often require excessive use of drape material, treatment of the drape material to make it fluid impervious and/or the use of additional layers of fluid impervious material to create the pockets.

An alternate solution has been to attach pouches to the drape to collect the fluids resulting from the operation. See for example the patent to Blanford (U.S. Pat. No. 3,452,750) wherein a pouch is used in conjunction with a vaginal bib to collect and measure fluids.

In surgical procedures which produce large quantities of fluids, larger bags or pouches oftentimes are used with additional material around the fenestration to aid in the control and direction of fluids into the bag. Examples of such embodiments include Morris (U.S. Pat. No. 4,169,472), Vinson (U.S. Pat. No. 4,559,937) and McAllester (U.S. Pat. No. 4,598,458). Morris uses a liquid impervious bag which is secured to the front surface of the drape. Two separate strips of material are then attached to the front surface of the drape, one on either side of the fenestration such that they have flap portions which are free of attachment from the drape. The respective bottom ends of the strips are then bent over upon themselves at an angle to form bent-over bottom ends which are tucked inside the open end of the bag and adhesively attached to the inside of the bag. During use of the drape, these flaps may be raised upwardly to a position which is at an angle to the upper surface of the main sheet. Vinson also uses a bag which is attached to the upper surface of the drape. In order to assist fluid run-off from the surgical site into the fluid collection bag, fluid control rails are located alongside but spaced from the fenestration and extend to the opening in the bag. When the bag and drape are in their normal operational position, fluid is blocked from flowing past the rails and is deflected and channeled into the fluid collection bag. In a preferred construction, the rails are constructed from lengths of flexible tubing encased in flexible sheet material with the sheet material being attached to the upper surface of drape. McAllester is another drape which uses a collection bag and the same rails disclosed in the Vinson reference.

A drawback with the above references is their inability to control heavy fluid flows and splashing due to their low height and/or lack of structural rigidity around the fenestration site. Another disadvantage is the cost and time involved in constructing multiple-piece drapes from various components. Such surgical drapes are one use items and as a result, cost is a critical factor. With such designs there is also an increased risk of leakage due to the number of contact and connection points which must be made in forming the drape and maintained during the use of the drape. Such drapes are subject to folding, unfolding and fair amounts of manipulation during their use, not to mention the stresses involved in retaining the collected fluids.

It is therefore an object of the present invention to provide a surgical drape which employs a fluid collection system with good integrity, and improved control, direction and retention of fluids produced during a surgical procedure.

These and other objects of the present invention will become more apparent upon a further review of the following specification, drawings and claims.

SUMMARY OF THE INVENTION

The present invention relates to a surgical drape with a fluid collection system for channeling and collecting fluids emanating from the surgical site during an operation. The surgical drape includes a main sheet with a fenestration to allow access to the surgical site. Attached to the main sheet is a fluid collection bag, made from a fluid impervious material such as plastic film. The fluid collection bag comprises a front panel and a rear panel joined along common side edges and defining a fluid receiving chamber therein with the open top end positioned adjacent the fenestration in the main sheet. Also formed from the front and rear panels are a pair of troughs which extend upwardly from the open top end of the fluid collection bag along the common side edges such that the troughs and the open top end of the bag surround at least a portion of the fenestration. The troughs are designed to open inwardly toward the fenestration so as to contain and channel fluids into the open top end of the fluid collection bag.

The fluid collection bag may be fitted with a sieve adjacent the opening to trap and collect objects such as instruments, sponges and bone fragments, which may fall into the bag during a surgical procedure. A drainage opening also may be placed in the bag to allow removal of fluids from the bag.

To keep the troughs and the fluid collection bag open during use, malleable opening strips may be attached to the inside or outside of the troughs and bag opening. Once the drape is in place, the malleable strips may be bent and shaped to maintain the troughs and the bag in an open position.

Each of the fluid troughs has an upper flap formed from the front panel of the fluid collection bag and a lower flap formed from the rear panel of the bag. If desired, the material of the rear panel and lower flaps may completely span the fenestration and surrounding area of the main sheet, in which case, the rear panel must have a fenestration which is in registry with the fenestration in the main sheet. With this design, the fluid impervious material of the rear panel completely surrounds the fenestration in the main sheet thereby reducing the risk of fluid leakage.

DESCRIPTION OF THE PREFERRED EMBODIMENT

Figure 1:
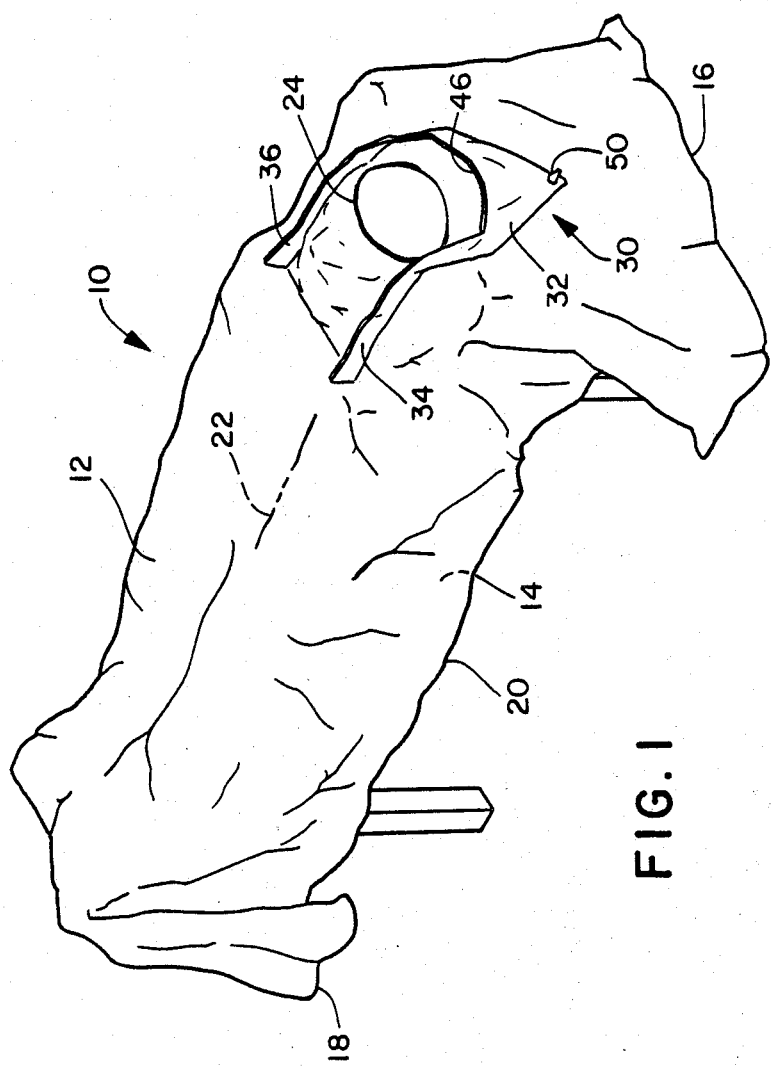
FIG. 1 is a perspective view of a surgical drape and fluid collection system according to the present invention positioned on the skull of a patient for a craniotomy.

Referring to FIGS. 1 through 4 there is shown a surgical drape or main sheet 10 with a fluid collection system 30. As shown in FIG. 1, the drape 10 is rectangular in shape with a front surface 12, a back or bottom surface 14, a top edge 16, a bottom edge 18 and a pair of opposed side edges 20 and 22. Disposed within the interior portion of the drape 10 is a fenestration 24 to provide access to the surgical site. If desired, an incise material 26 (FIG. 3) may be attached to the back 14 of the drape 10, over the fenestration 24 and the surrounding area. Alternatively, the incise material may be positioned over the top of the fenestration 24 or sandwiched between the layers of material of the fluid collection system 30. Such incise materials typically have an adhesive backing and a removable cover. As the drape 10 is being positioned on the patient, the removable cover is peeled off and the adhesive side of the incise material is secured to the patient. As will be apparent to those skilled in the art, drape designs are readily modified to meet the needs of the particular surgical procedures. For example, leg and/or arm board covers may also be incorporated into the drape construction. As a result, other drape configurations and attachments as well as other fenestration shapes and locations are also contemplated to be within the scope of the present invention. The embodiment used for the illustration of applicants' invention within the present set of figures is a craniotomy sheet.

The drape 10 itself may be made from any number of materials and combinations thereof. Breathable materials such as woven and nonwoven materials may be used in the construction of the drape 10. Such materials are desirable in that they are breathable and therefore allow air circulation and provide an added degree of comfort to the patient. A particularly well-suited nonwoven material for use in drapes is a spunbond/meltblown/spunbond laminate material available from the Kimberly-Clark Corporation and sold under the trademark Evolution ™ Fabric System. Such material provides an added advantage in that it contains a bacterial barrier between the top 12 and the bottom 14 of the sheet 10 due to the microfibrous inner meltblown layer. Alternatively, a fluid impervious material such as plastic film may be used as the sheet material or a combination of nonwoven and film materials may also be used. For example, the drape, as a whole, may be made from a breathable nonwoven material and the area surrounding the fenestration may be made fluid impervious by adding a layer of plastic film or by treating the nonwoven material with a coating of fluid impervious material such as latex.

The fluid collection system 30 is constructed from a fluid impervious material. Thermoplastic films including polyurethane, polyethylene and ethylene vinyl acetate are examples of such materials. The advantages of such materials include their ability to be heat sealed and sterilized. To this end the material selected must be able to withstand the temperatures and gases used during the sterilization process which includes temperatures in excess of 140° F. for ethylene oxide sterilization. With steam sterilization, temperatures range from 250° to 270° F. A particularly well suited film material for ethylene oxide sterilization is polyethylene.

Figure 2:
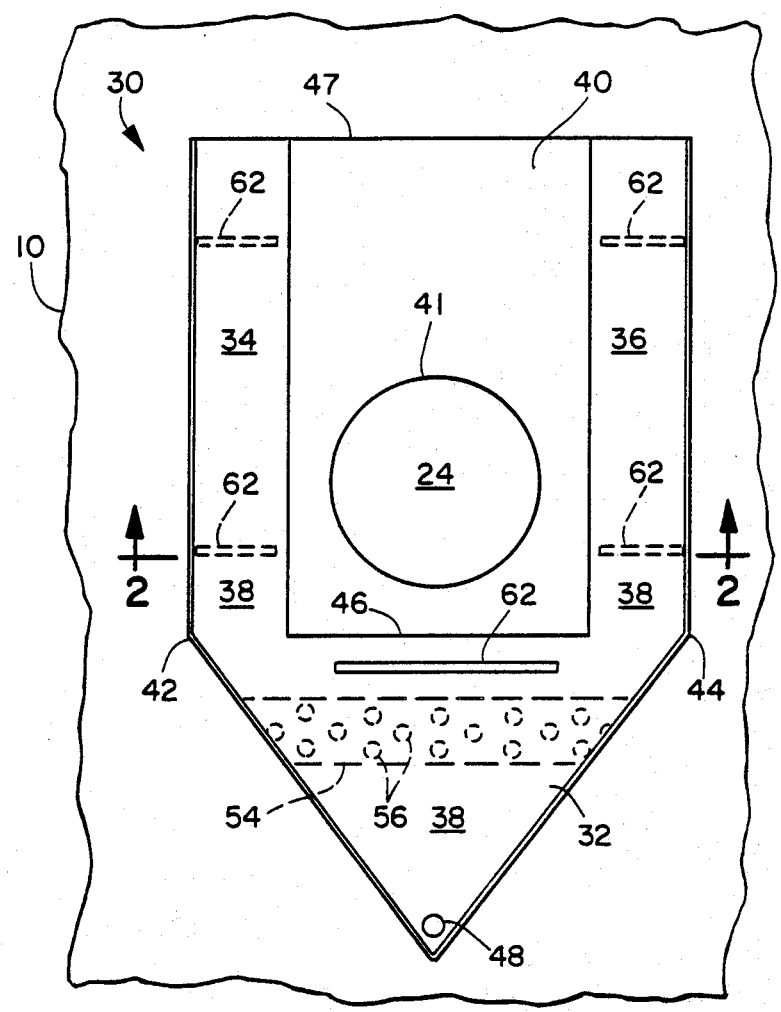
FIG. 2 is a top plan view of a surgical drape and fluid collection system according to the present invention.

Referring to FIGS. 1 through 4, the fluid collection system 30 is attached to the front surface 12 of drape 10 and includes a fluid collection bag 32 with a pair of fluid collection troughs (left trough 34 and right trough 36) which are integrally formed with the fluid collection bag 32. Referring to FIG. 2, the fluid collection bag 32 is positioned about the fenestration 24 so that the left and right troughs 34 and 36 extend above the top most portion of the fenestration 24 and the bag 32 is positioned in the path of fluid run-off. In this way, as fluids emanate from the fenestration, the left and right troughs direct the fluid flow into the bag 32, thereby preventing unrestricted fluid run-off. A practical illustration of this is shown in FIG. 1. The fenestration 24 is positioned over the cranium of the patent and the fluid collection bag 32 is allowed to hang down below the operation site. As fluids are released, the troughs 34 and 36 channel the fluids into the fluid collection bag 32.

The advantages of the present invention stem from the one piece design of the fluid collection system 30. First, because the fluid collection system 30 is a one piece item, it can be applied to virtually any design of drape by simply adhering or attaching it to the drape so that the bag 32 and troughs 34 and 36 surround the major portion of the fenestration. The fluid collection system 30 may be attached to the drape 10 in any number of ways, the two most advantageous being adhesives and heat sealing. Once the fluid collection system is in place, its simple design and inherent integrity provide a means for effectively channeling fluids into the bag 32. Unlike other designs, the present invention has no separate pieces which can become misaligned or detached thereby creating a risk of fluid spilling over onto other areas of the patient, the surgical team or the operating floor. Such hazards are especially apparent when the surgical procedure requires frequent movement and repositioning of the patient and thus the drape as for example in an arthroscopy.

Figure 3:
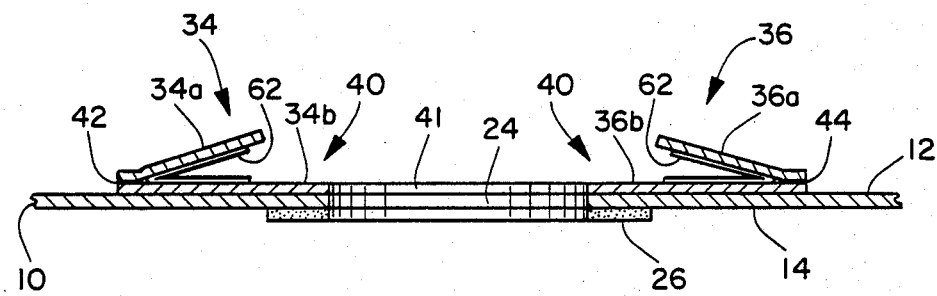
FIG. 3 is a cross-sectional view of the surgical drape and fluid collection system of FIG. 2 taken along line 2—2 of FIG. 2.
Figure 4:
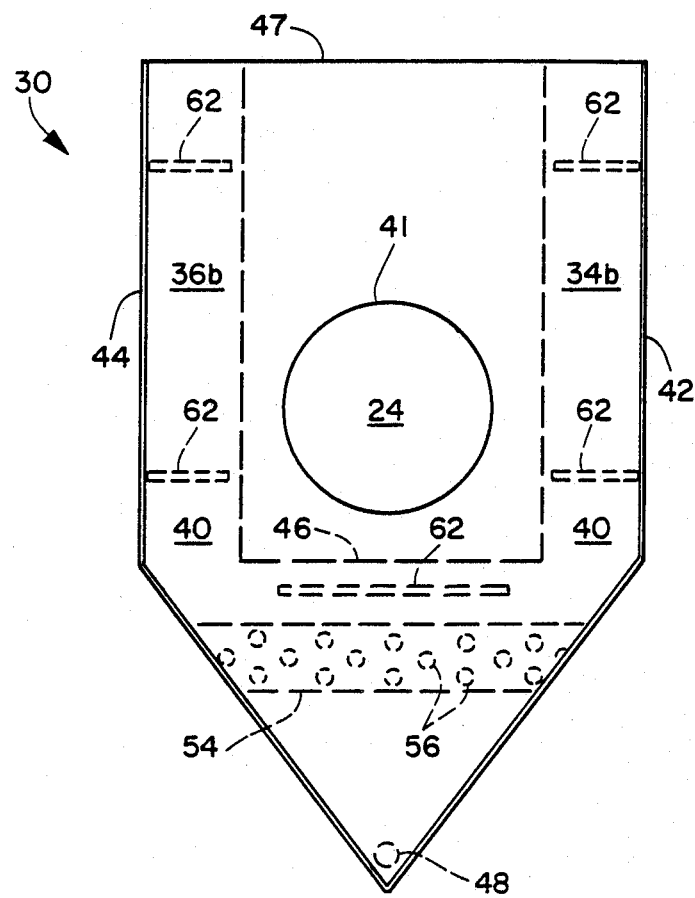
FIG. 4 is a bottom view of the fluid collection system depicted in FIG. 2.

Referring to FIGS. 2 through 4, the fluid collection bag 32 is triangular in shape and has a front panel 38 and rear panel 40 joined along common side edges (left and right) 42 and 44 to define a fluid receiving chamber with an open end 46 positioned adjacent the fenestration 24. The face 38 of the fluid collection bag 32 is a one piece construction wherein the front 38 of the collection bag 32 and the left and right troughs 34 and 36 are integrally formed from the same piece of material. To form the troughs 34 and 36 and to allow access to the fenestration 24 in the drape 10, the front panel 38 has a rectangular or "U" shaped cut-out portion extending from a point on the top edge 47 of the bag 32 interior the closed left edge 42 down along and inside the left edge 42, across to a point interior the closed right edge 44 and up along and inside the closed right edge 44 to another point on the top edge 47 interior to the closed right edge 44, thereby defining the left trough 34 and the right trough 36.

Turning to FIG. 3, the left and right troughs 34 and 36 each have an upper flap (34a and 36a) which are part of front panel 38 and a lower flap (34b and 36b) which are part of the rear panel 40. Upper and lower flaps 34a and 34b are joined along common edge 42 while upper and lower flaps 36a and 36b are joined along common edge 44. In the embodiment shown in FIGS. 2 and 4, the lower flaps 34b and 36b actually extend all the way across the fenestration 24 in drape 10. As a result, the rear panel 40 has a fenestration 41 which is in registry with the fenestration 24 in drape 10. In this way, the entire area between the troughs 34 and 36 and surrounding the fenestration 24 of drape 10 is completely covered in fluid impervious material. This one piece design gives strength to the trough/bag construction and allows the fluid collection system 30 to be attached to the drape 10 as a single unit which facilitates assembly. The fluid collection system 30 may be attached to the drape 10 in any number of ways, the two most advantageous being adhesives and heat sealing.

The collection bag 32 shown in the figures is triangular in shape and has a drainage opening 48 fitted with a drain nozzle 50 located in the bottom-most portion of the bag 32. This triangular design is the most advantageous since it directs the fluids collected within the bag 32 to a point adjacent the drain opening 48 thereby allowing the majority of the fluid to be drained from the bag 32 if so desired. Note, however, that other shapes and sizes of bags, rectangular bags for example, also may be used in conjunction with the present invention. The actual size and shape of the bag will be governed primarily by the end use of the drape. In operations which generate large amounts of fluids, such as craniotomies, larger bags may be desirable. However, it should be understood that as the fluid level in the bag increases, so does the weight. This in turn may result in the bag and entire drape slipping off the patient at some point during the procedure. In such cases it may be desirable to either periodically or continuously drain the fluids from the bag.

Figure 5:
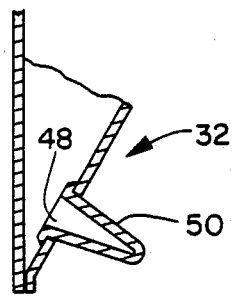
FIG. 5 is a cross-sectional side view of a drainage nozzle which may be used in conjunction with the surgical drape and fluid collection system of the present invention.
Figure 6:
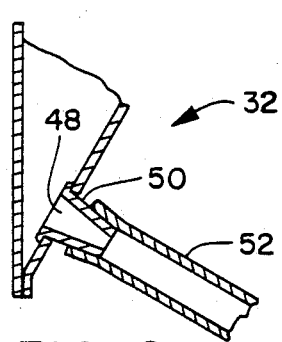
FIG. 6 is another cross-sectional side view of the drainage nozzle depicted in FIG. 5. In this depiction the drainage nozzle is shown with its tip removed and a piece of flexible tubing positioned over the outside of the nozzle to permit the drainage of fluids from the fluid collection system.

Referring to FIGS. 5 and 6, the end of drain nozzle 50 may be cut off and a length of flexible tubing 52 may be slid over the end. The other end of the flexible tubing 52 then may be placed into an auxiliary fluid containment vessel such as a bucket (not shown) positioned underneath the operating table. Alternatively, a shut-off valve (not shown) may be built into the drain nozzle 50 or inserted into the tubing 52 at some point to control fluid release from the bag 32.

During an operation, many instruments, sponges, etc., are used. At the end of the operation, all such items must be collected and counted as a precautionary measure to ensure that none of them are left within the body cavity. Should any of these items fall into the fluid collection bag 32, they could block the drain opening 48 and their removal from the fluid collection bag 32 might prove difficult and/or dangerous. As a result, the fluid collection bag 32 may be provided with a sieve 54 to trap objects which might find their way into the bag. This sieve 54 is shown in phantom in FIGS. 2, 4, 7 and 9 and in cross-section in FIG. 11.

Figure 11:
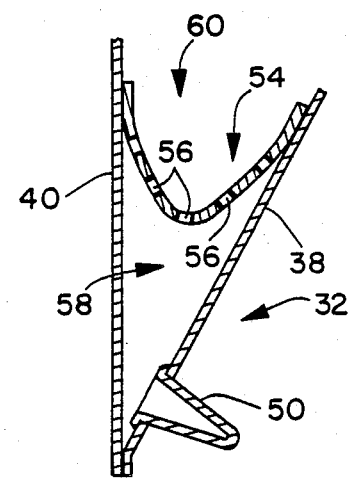
FIG. 11 is a cross-sectional side view of the sieve portion of a fluid collection system according to the present invention.
Figure 9:
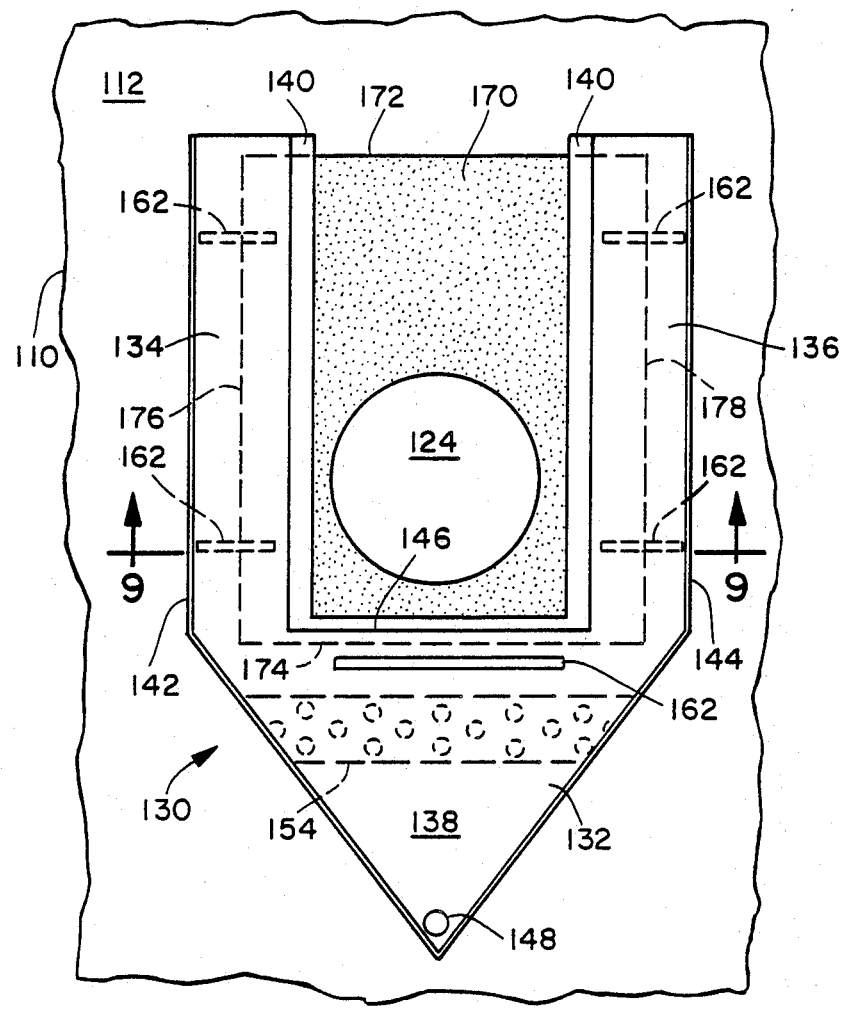
FIG. 9 is a top plan view of a further embodiment of a surgical drape and fluid collection system according to the present invention.

Turning to FIGS. 2 and 11, the sieve 54 is positioned inside the fluid collection bag 32 adjacent the opening 46. The sieve 54 has a plurality of perforations, slits or small holes 56 to allow the passage of fluids into the lower portion 58 of the bag 32 while retaining solid objects such as instruments, sponges, tissue and bone fragments within the upper portion 60. The sieve 54 is connected to the front panel 38, rear panel 40 and edges 42 and 44 of fluid collection bag 32, preferably by heat sealing or other suitable means which will permit the sieve 54 and bag 32 to expand and remain open during use.

To keep the bag 32 and the troughs 34 and 36 open during use, malleable opening means or strips 62 may be attached to the troughs 34 and 36 and the open end 46 of bag 32. The malleable strips 62 may be made from any number of materials such as plastic, metal or plastic coated metal. The primary attributes of the material are that it is moldable, noncorrosive, sterilizable and readily attachable to the material chosen for the fluid collection system 30. While the strips 62 may be attached to the fluid collection system 30 in any number of ways and positions, in the preferred embodiment, the strips 62 in the troughs 34 and 36 are folded into a "V" shape and attached to the interior surfaces of the troughs 34 and 36 by adhesives or other means. Once the drape 10 is in place on the patient, the open ends of the "V's" of the malleable strips 62 can be spread apart to keep the troughs open. The malleable strip 62 located parallel to the open end 46 of bag 32 is initially a flat strip. Once the drape 10 is in place, the strip 62 may be bent or formed into a convex or half-moon shape to keep the front panel 38 of the open end 46 of the bag 32 spaced apart from the rear panel 40. Thus, these malleable strips 62 permit the troughs 34 and 36 and the opening 46 in the bag 32 to remain open, thereby reducing the chance of fluid spilling and splash-over onto unintended areas of the drape 10 and the general operating area.

Figure 7:
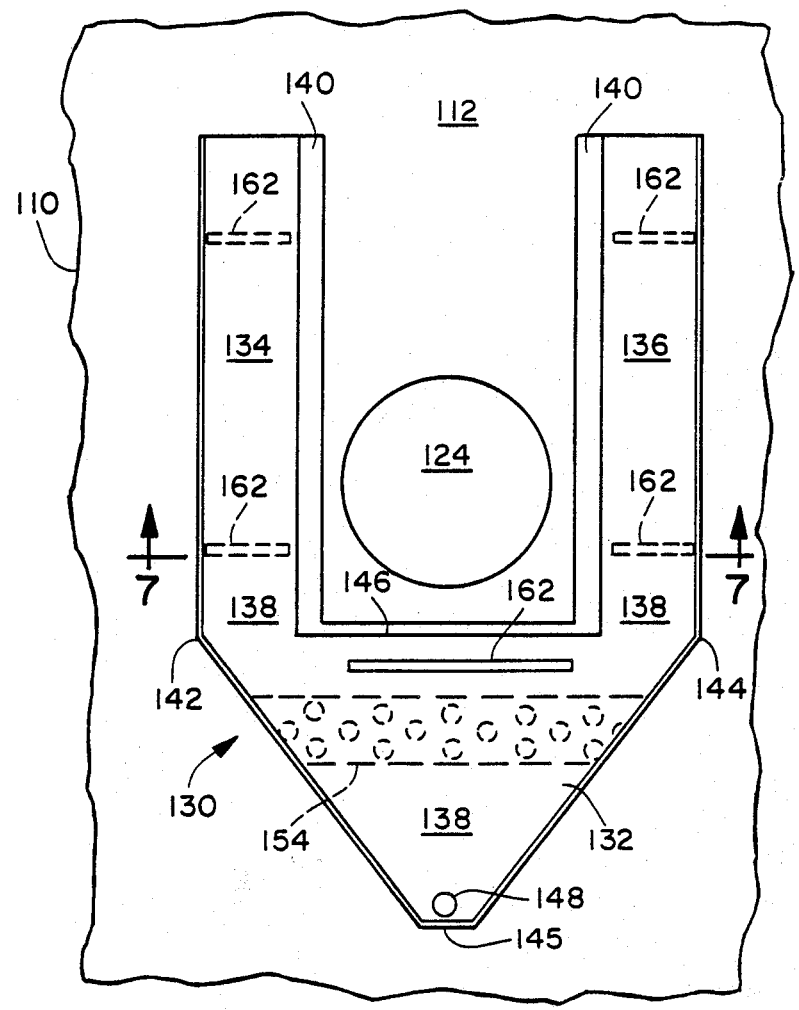
FIG. 7 is a top plan view of another embodiment of a surgical drape and fluid collection system according to the present invention.
Figure 8:
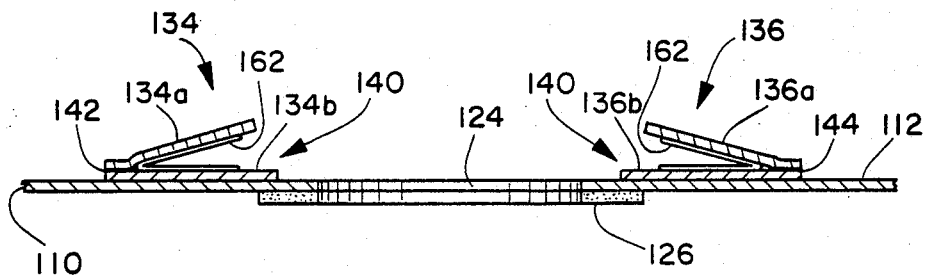
FIG. 8 is a cross-sectional view of the surgical drape and fluid collection system of FIG. 7 taken along line 7—7 of FIG. 7.

Another embodiment of the present invention is shown in FIGS. 7 and 8. Once again the fluid collection system 130 attached to the drape 110 includes a fluid collection bag 132 having a pair of fluid troughs (left and right) 134 and 136 integrally formed therewith. The fluid collection bag 132 has a front panel 138 and a rear panel 140 joined along common side edges 142 and 144 and a bottom edge 145 with an open end 146 positioned adjacent the fenestration 124 in the drape 110. As with the embodiment shown in FIGS. 2 through 4, the fluid collection system may be fitted with a drain opening 148, a sieve 154 and malleable opening means or strips 162. The difference in the configuration shown in FIGS. 7 and 8 as compared to the one shown in FIGS. 2 through 4 resides in the rear panel 140 of the fluid collection system 130.

Referring to FIGS. 7 and 8, the rear panel 140 has a shape and cut out portion similar to that of front panel 138. The rear panel 140 has a one piece construction including lower trough flaps 134b and 136b which are joined to upper flaps 134a and 136a along common edges 142 and 144. Unlike the configuration shown in FIGS. 2 through 4, the material of rear panel 140 does not extend all the way across the fenestration 124. Instead, the rear panel 140 has a rectangular or "U" shaped cut out portion and thus, the troughs 134 and 136 straddle opposed sides of the fenestration 124. The rear panel 140, including the lower flaps 134b and 136b of troughs 134 and 136 may be attached to the front surface 112 of the drape 110 with adhesives or by heat sealing. Because the rear panel 140 does not completely span the fenestration 124 and surrounding area, care should be taken to assure a good seal between the fluid collection system 130 and the drape 110 so that no fluid will leak between the two surfaces. As with other embodiments, fluid impervious materials such as plastic films are the most preferred materials of construction for the fluid collection system 130. Additionally, an incise material 126 may be used with the drape 110.

Figure 10:
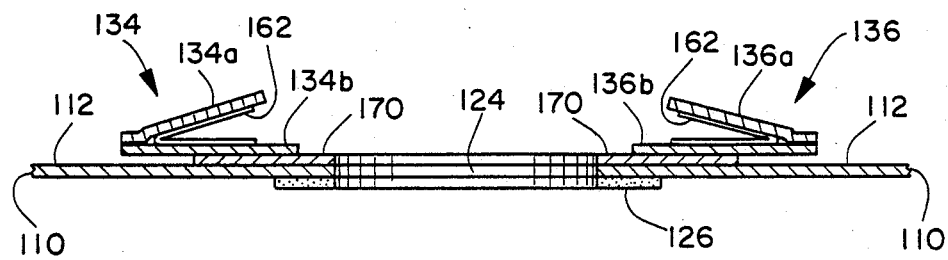
FIG. 10 is a cross-sectional view of the surgical drape and fluid collection system of FIG. 9 taken along line 9—9 of FIG. 9.

As can be seen from FIG. 7, the area surrounding the fenestration between the two troughs 134 and 136 is not covered by the fluid impervious material. As a result, when the drape 110 itself is not fluid impervious it may be desirable to place an additional layer 170 of material between the top surface 112 of the drape 110 and the fluid collection system 130. See FIG. 9. This layer 170 may be a layer of fluid-impervious material or an absorptive material such as a layer of foam having a top edge 172, a bottom edge 174 and a pair of side edges, 176 and 178. As shown in FIG. 10, the foam layer 170 may be placed behind the fluid collection system 130. Alternatively, the bottom edge 174 and the side edges 176 and 178 may be tucked inside the fluid collection system 130 such that these edges overlap the interior edges of the rear panel 140 including the troughs 134 and 136 which surround the fenestration 124. The advantage of the foam is its absorptive characteristics which reduces splashing and therefore aids in the channeling and collection of fluids.

Referring again to FIGS. 1 through 4, in use the sterilized drape 10 is placed over the patient such that the fenestration 24 is centered over the incision area and such that the fluid collection bag 32 is positioned in the expected path of fluid run-off. The drape used for illustrative purposes in FIGS. 1 through 4 is a craniotomy sheet. As shown in FIG. 1, this specific sheet would be placed on the patient such that the fenestration 24 was centered on the skull of the patient with the fluid collection bag 32 hanging below the patient's head. Should the sheet contain an incise material 26, the releasable backing material would first be removed from the incise material prior to its attachment to the skull. One particular advantage is using incise material with the present invention is that it serves to anchor the sheet to the patient which helps prevent shifting or slipping of the drape during the operation. In addition to or in lieu of the incise material 26, a pressure sensitive adhesive may be applied to the back 14 of the drape 10 to further secure the drape 10 to the patient. As an added precaution against slipping, it also may be advisable to secure the sheet to the surgical table at other locations with, for example, clamps. Otherwise, the weight of the fluid in the collection bag 32 may cause the drape 10 to slip and fall to the floor which, under sterile practices, would require that a new sterile sheet be used to cover the operating site.

Once the drape is in place, the front panels 34 and 36 and the open end 46 of fluid collection bag 32 may be opened and maintained in the open position with the aid of the malleable strips 62. In so doing, fluids from the operation will be channeled into the fluid collection bag 32 where they may be stored or removed via drain opening 48.

The advantages of the present invention stem from the unique one piece nature of the fluid collection system. The integral troughing and collection system provides effective lateral barriers to fluid run-off and also provides an efficient means for channeling fluids into the fluid collection bag. As described in the preceding portions of the application, the fluid collection system has a front panel and a rear panel. These panels may be separate pieces which are joined at their edges. Alternatively, the fluid collection system may be formed from a single piece of material which is folded over and then sealed, thereby reducing the number of seams which must be closed in order to form a fluid-tight construction.

While the foregoing description of the present invention has been in the form of a craniotomy sheet, this is for illustration purposes only. It should be readily understood that the scope of the present invention is intended to cover all such surgical drapes wherein a fluid channeling and collection system is needed. It will also be readily appreciated by those skilled in the art that other modifications and changes may be made to the present invention without departing from the scope and spirit of the following claims.

I claim:

1. A surgical drape for channeling and collecting fluids comprising:
   a main sheet having a front surface, a back surface, a top edge and a bottom edge joined by a pair of opposed side edges and a fenestration located therein, and
   a fluid collection bag for receiving such fluids attached to said front surface of said main sheet, said fluid collection bag having a front panel and a rear panel joined along common side edges and defining a fluid receiving chamber therein with an open top end positioned adjacent said fenestration in said main sheet,
   said front and rear panels further forming a trough on either side of said bag extending upwardly from said open top end along said common side edges of said bag and being integrally formed therewith, each trough having an upper flap formed from said front panel and a lower flap formed from said rear panel, said upper and lower flaps being joined along a common edge such that said troughs and said open top end of said bag surround at least a portion of said fenestration, said troughs opening inwardly toward said fenestration so as to contain and channel such fluids into said open top of said fluid collection bag.

2. A surgical drape according to claim 1 which further includes a drainage opening located in said fluid collection bag.

3. A surgical drape according to claim 1 which further includes a sieve located within said fluid collection bag adjacent said open top end.

4. A surgical drape according to claim 1 wherein said troughs contain malleable opening means to maintain said troughs is an open position for channeling said fluids into said fluid collection bag.

5. A surgical drape for channeling and collecting surgical fluids comprising:
   a main sheet having a front surface, a back surface, a top edge and bottom edge joined by a pair of opposed side edges and fenestration located therein, and
   a fluid collection bag for receiving said fluids having a front panel and a rear panel joined along common side edges and defining a fluid receiving chamber therein with an open top end positioned adjacent said fenestration is said main sheet,
   said front and rear panels further forming a trough on either side of said fluid collection bag extending upwardly from said open top end along said common side edges of said fluid collection bag and be integrally formed therewith, each trough having an upper flap formed from said front panel and a lower flap formed from said rear panel, said upper and lower flaps being joined along a common edge such that said troughs and said open top end of said fluid collection bag surround at least a portion of said fenestration, said troughs opening inwardly toward said fenestration so as to contain and channel said fluids into said open top of said fluid collection bag,
   a drainage port located in said fluid collection bag,
   a sieve located within said fluid collection bag adjacent said open top end, and
   malleable opening means attached to said troughs to maintain said troughs in an open position for channeling said fluids into said fluid collection bag.

6. A surgical drape for channeling and collecting surgical fluids comprising:
   a main sheet having a front surface, a back surface, a top edge and bottom edge joined by a pair of opposed side edges and a fenestration located therein,
   a fluid collection bag for receiving said fluids attached to said front surface of said main sheet,
   said fluid collection bag having a front panel and a rear panel joined by a closed left edge, a closed bottom edge, a closed right edge and further having an open top thereby defining a fluid chamber for receiving said fluids,
   said rear panel having a fenestration in registry with said fenestration in said main sheet,
   said front panel having a cut-out portion extending downwardly from a first point on said open top interior to and along said closed left edge to a second point intermediate said open top and said closed bottom edge, across to a third point interior to said closed right edge and upwardly along and interior to said closed right edge to a fourth point on said open top interior to said closed right edge thereby forming a pair of spaced apart troughs, each trough having an upper flap formed from said front panel opening inwardly toward said fenestration for containing a channeling said fluids into said fluid collection bag.

* * * * *

UNITED STATES PATENT AND TRADEMARK OFFICE
CERTIFICATE OF CORRECTION

PATENT NO. : 4,890,628

DATED : January 2, 1990

INVENTOR(S) : Elizabeth M. Jackson

It is certified that error appears in the above-identified patent and that said Letters Patent is hereby corrected as shown below:

Column 8, line 27, "is using " should read --of using--

Column 9, line 40, "troughs is" should read --troughs in--.

Column 10, line 2, "fenestration is" should read --fenestration in--.

Column 10, line 6, "be" should read --being-- and

Column 10, line 48, "containing a" should read --containg and --.

Signed and Sealed this

Ninth Day of March, 1993

*Attest:*

STEPHEN G. KUNIN

*Attesting Officer*     Acting Commissioner of Patents and Trademarks